(12) United States Patent
Yokobayashi

(10) Patent No.: US 12,085,550 B2
(45) Date of Patent: Sep. 10, 2024

(54) DEVICE FOR TESTING SOLUBILITY OF DRUGS IN GASTROINTESTINAL TRACT

(71) Applicant: HITACHI ZOSEN CORPORATION, Osaka (JP)

(72) Inventor: Takayasu Yokobayashi, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 407 days.

(21) Appl. No.: 17/610,859

(22) PCT Filed: Apr. 30, 2020

(86) PCT No.: PCT/JP2020/018327
§ 371 (c)(1),
(2) Date: Nov. 12, 2021

(87) PCT Pub. No.: WO2020/230656
PCT Pub. Date: Nov. 19, 2020

(65) Prior Publication Data
US 2022/0260544 A1    Aug. 18, 2022

(30) Foreign Application Priority Data
May 15, 2019 (JP) ................................. 2019-091778

(51) Int. Cl.
G01N 33/15 (2006.01)
(52) U.S. Cl.
CPC .................................. G01N 33/15 (2013.01)
(58) Field of Classification Search
None
See application file for complete search history.

(56) References Cited

U.S. PATENT DOCUMENTS

| | | |
|---|---|---|
| 5,807,115 A | 9/1998 | Hu |
| 9,285,353 B1 * | 3/2016 | Hughes .................. G01N 33/15 |

(Continued)

FOREIGN PATENT DOCUMENTS

| | | |
|---|---|---|
| CN | 201344926 Y | 11/2009 |
| CN | 105003372 A | 10/2015 |

(Continued)

OTHER PUBLICATIONS

International Search Report dated Jul. 7, 2020, issued in corresponding International Application No. PCT/JP2020/018327 with English translation (4 pgs.).

(Continued)

*Primary Examiner* — Peter J Macchiarolo
*Assistant Examiner* — Jermaine L Jenkins
(74) *Attorney, Agent, or Firm* — Pillsbury Winthrop Shaw Pittman, LLP

(57) ABSTRACT

Provided is a device for testing solubility of drugs in gastrointestinal tract. The device for testing solubility includes: a plurality of vessels respectively corresponding to gastrointestinal tract of a living body; digestive juice supply devices supplying digestive juice to the vessel requiring the supply of the digestive juice; liquid delivery paths each being provided between the vessels and extending from an upstream-side vessel to a downstream-side vessel; delivery driving sources applying a fluid force to a mixed liquid of the digestive juice and an oral drug in the liquid delivery paths; and a control device controlling delivery speeds of the delivery driving sources according to a temporal change of a flow rate from an upstream side to a downstream side of the gastrointestinal tract of the living body.

11 Claims, 3 Drawing Sheets

(56) References Cited

U.S. PATENT DOCUMENTS

| | | | |
|---|---|---|---|
| 10,234,467 B2 * | 3/2019 | Merchant | ............... G01N 33/84 |
| 2003/0088369 A1 | 5/2003 | Hughes | |
| 2012/0034704 A1 | 2/2012 | Hughes et al. | |
| 2021/0381590 A1 | 12/2021 | Weinhardt | |

FOREIGN PATENT DOCUMENTS

| | | |
|---|---|---|
| CN | 105674683 A | 6/2016 |
| CN | 207586195 U | 7/2018 |
| CN | 108533435 A | 9/2018 |
| CN | 108678881 A | 10/2018 |
| CN | 109563927 A | 4/2019 |
| JP | 2003149229 A | 5/2003 |
| JP | 3787322 B2 | 6/2006 |
| JP | 2012037512 A | 2/2012 |

OTHER PUBLICATIONS

1st Examination Report dated Feb. 11, 2023, issued in corresponding Chinese Patent Application No. 202080035000.9 with English translation (19 pgs.).

"Lamb Dysentery", Li Zhaojia, pp. 16-18, Gansu People's Publishing House, 1979, with English language summary (9 pgs.).

* cited by examiner

DEVICE FOR TESTING SOLUBILITY OF DRUGS IN GASTROINTESTINAL TRACT

CROSS-REFERENCE TO RELATED APPLICATIONS

This application is a national stage entry of PCT/JP2020/018327, filed Apr. 30, 2020, which claims priority to Japanese Application No. 2019-091778, filed May 15, 2019, the contents of each of which are herein incorporated by reference in their entireties.

TECHNICAL FIELD

The present invention relates to a device for testing solubility of drugs in gastrointestinal tract and particularly relates to a device for testing solubility of drugs in vitro.

BACKGROUND ART

A known device for testing solubility of drugs in gastrointestinal tract is provided with a plurality of vessels that contain artificial digestive juices respectively corresponding to gastrointestinal tract of a living body. With the vessels in the known device for testing solubility, degrees of solubility of drugs and a pH of digestive juice containing dissolved drugs can be examined with time in order to check a state of dissolution of drugs such as tablets administered into a human mouth or study the process of absorbing medicinal properties.

However, vessels in the known device are independent of one another and are not linked to one another. This makes a deviation from conditions in an actual living body.

In order to solve the problem, JP3787322B proposes a device including a stomach chamber, an intestine chamber, and a circulation chamber that are connected in series and a pump for delivering liquids from the chambers into different chambers. Moreover, JP3787322B describes a method of analyzing liquids, a method of calculating the volume of liquid in the chamber, and a method of calculating a flow rate during the delivery of liquid.

SUMMARY OF INVENTION

Technical Problem

An object of the present invention is to more accurately test solubility of drugs by improving the technique of JP3787322B so as to more correctly simulate the gastrointestinal tract of a living body, e.g., a human being.

Solution to Problem

In order to attain the object, a device for testing solubility of drugs in gastrointestinal tract according to the present invention includes:
  a plurality of vessels respectively corresponding to gastrointestinal tract of a living body;
  a digestive-juice supply device supplying digestive juice to at least one of the vessels requiring supply of the digestive juice;
  a liquid delivery path provided between the vessels and extending from the vessel on an upstream-side to the vessel on a downstream-side;
  a delivery driving source applying a fluid force to a mixed liquid of the digestive juice and an oral drug in the liquid delivery path; and
  a control device controlling the delivery speed of the delivery driving source according to a temporal change of a flow rate from an upstream side to a downstream side of the gastrointestinal tract of the living body.

According to the device for testing solubility of drugs in gastrointestinal tract of the present invention, it is preferable that the device further include a suction nozzle that communicates with the liquid delivery path and is opened at a bottom of the upstream-side vessel so as to be able to fully deliver the oral drug in the upstream-side vessel into the downstream-side vessel.

According to the device for testing solubility of the present invention, it is preferable that the control device control the delivery speed of the delivery driving source according to a temporal change of a speed of excretion from the gastrointestinal tract of the living body.

According to the device for testing solubility of the present invention, it is preferable that the control device control an amount of liquid in each of the vessels with time by controlling the delivery speed of the delivery driving source.

According to the device for testing solubility of the present invention, it is preferable that the device further include a liquid amount sensor for detecting the amount of liquid in each of the vessels.

According to the device for testing solubility of the present invention, it is preferable that a most downstream vessel be provided with a drain device for controlling an amount of liquid in the most downstream vessel with time.

According to the device for testing solubility of the present invention, it is preferable that the control device determine presence or absence of trouble in the device based on the amount of liquid in each of the vessels.

According to the device for testing solubility of the present invention, it is preferable that the control device be capable of inputting, as a test condition, an offline calculation result of at least one of the amount of liquid in each of the vessels, a pH value in each of the vessels, and a flow rate from the upstream side to the downstream side.

According to the device for testing solubility of the present invention, it is preferable that
  the device further includes a delivery speed detector for detecting the delivery speed of the delivery driving source, and
  the control device controls the delivery speed of the delivery driving source based on a detection result obtained by the delivery speed detector.

According to the device for testing solubility of the present invention, it is preferable that
  the device further includes an agitator for agitating liquid in each of the vessels, and
  the agitator be relocatable according to a change of the amount of liquid in each of the vessels.

According to the device for testing solubility of the present invention, it is preferable that a vessel corresponding to a small intestine of the living body contain a liquid having an organic phase and an aqueous phase, the vessel corresponding to the small intestine be provided with an agitator for agitating the liquid in the vessel, the agitator include an organic-phase paddle and an aqueous-phase paddle, and the organic-phase paddle be a floating paddle.

According to the device for testing solubility of the present invention, it is preferable that the device further include a netlike storage device, and the storage device containing a drug to be undissolved in a stomach of the living body immerse the drug into the digestive juice in a vessel corresponding to a stomach of the living body, the storage device containing the drug convey the drug from the vessel corresponding to the stomach of the living body to a vessel corresponding to a small intestine of the living body, and then the storage device immerse the drug into the digestive juice in the vessel corresponding to the small intestine of the living body.

Advantageous Effect of Invention

The device for testing solubility of drugs in gastrointestinal tract according to the present invention controls the delivery speed of the delivery driving source for applying a fluid force to a mixed liquid of the digestive juice and an oral drug in the liquid delivery path between the vessels, the delivery speed being controlled according to a temporal change of a flow rate from the upstream side to the downstream side of the gastrointestinal tract of the living body. This can more correctly simulate the gastrointestinal tract of the living body, e.g., a human being and more accurately test the solubility of the drugs.

DESCRIPTION OF EMBODIMENT

Figure 1:
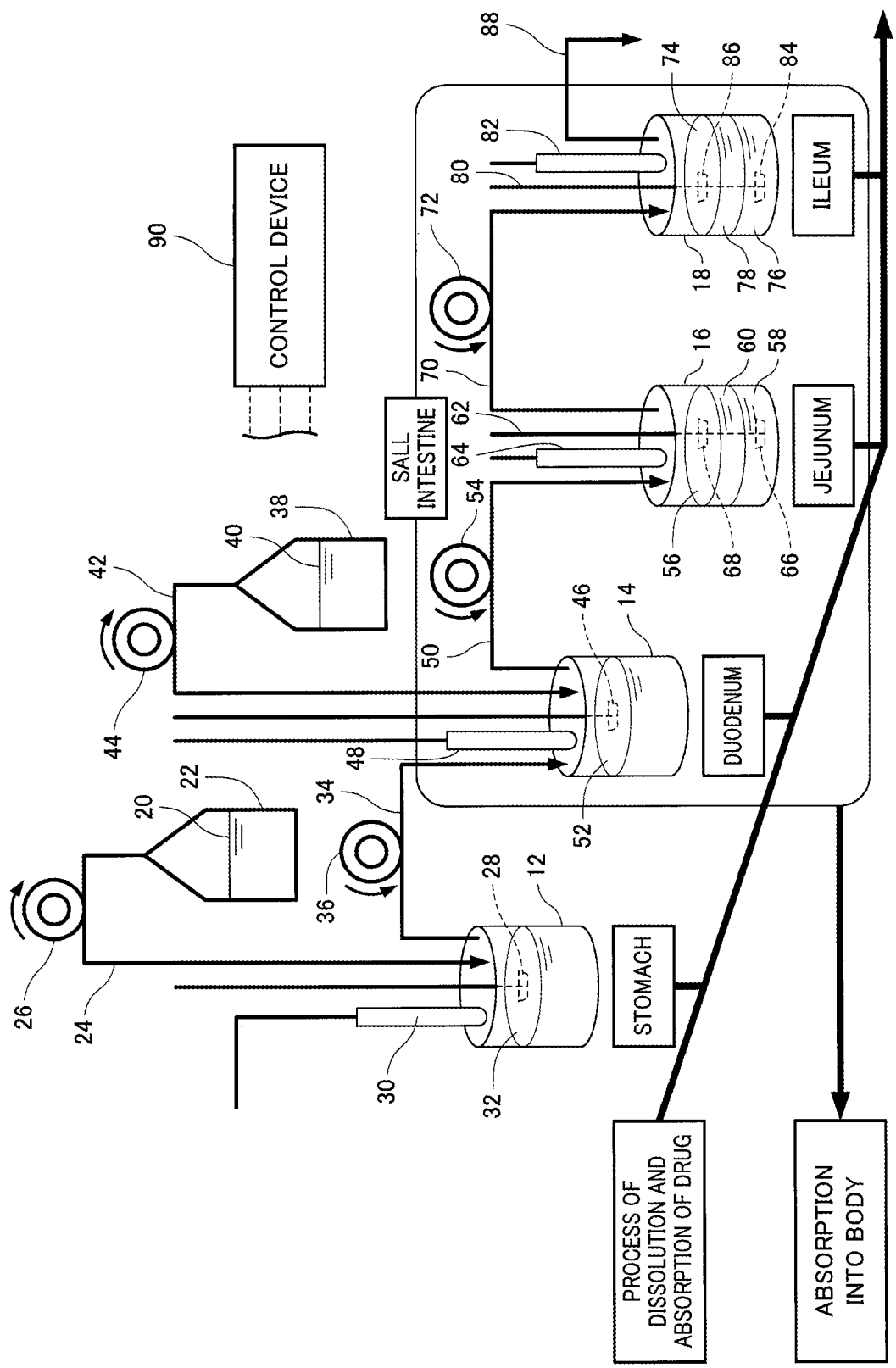
FIG. 1 illustrates a configuration of a device for testing solubility of drugs in gastrointestinal tract according to an embodiment of the present invention.

FIG. 1 illustrates a device for testing solubility of drugs in gastrointestinal tract according to an embodiment of the present invention. The device includes a plurality of vessels 12, 14, 16, and 18 respectively corresponding to gastrointestinal tract of a human being as a living body. The vessel 12 constitutes a stomach chamber, the vessel 14 constitutes a duodenum chamber, the vessel 16 constitutes a jejunum chamber, and the vessel 18 constitutes an ileum chamber. The duodenum, the jejunum, and the ileum can be collectively called "the small intestine."

The vessel 12 constituting the stomach chamber receives an artificially adjusted gastric juice 20. Reference numeral 22 denotes a vessel for storing the gastric juice 20, and reference numeral 24 denotes a supply path for the gastric juice from the vessel 22 for storage to the vessel 12 constituting the stomach chamber. The supply path 24 is provided with a peristaltic pump 26. These constituent elements constitute a digestive-juice supply device. The vessel 12 is provided with an agitator 28 and a pH sensor 30.

In the device of the present invention, oral drugs in the forms of tablets or capsules are charged into the gastric juice 20 in the vessel 12 constituting the stomach chamber. Thus, the vessel 12 constituting the stomach chamber contains a liquid 32 that is a mixture of the gastric juice 20 and the oral drugs. A supply path 34 is provided as a liquid supply path for supplying the liquid 32 into the vessel 14 constituting the duodenum chamber. The supply path 34 is provided with a peristaltic pump 36 acting as a delivery driving source.

To the vessel 14 constituting the duodenum chamber, a supply path 42 for supplying intestinal juice 40 from a storage vessel 38 into the vessel 14 is guided. The supply path 42 is provided with a peristaltic pump 44. These constituent elements also constitute a digestive-juice supply device. The vessel 14 is provided with an agitator 46 and a pH sensor 48 like the vessel 12 constituting the stomach chamber.

Reference numeral 50 denotes a supply path serving as a liquid supply path. The supply path 50 is provided to supply a liquid 52 in the vessel 14 constituting the duodenum chamber to the vessel 16 constituting the jejunum chamber. The supply path 50 is provided with a peristaltic pump 54.

A liquid 56 in the vessel 16 constituting the jejunum chamber is separated into an aqueous phase 58 and an oil phase 60 serving as an organic phase. The vessel 16 is similarly provided with an agitator 62 and a pH sensor 64. The agitator 62 includes an aqueous phase paddle 66 for agitating the aqueous phase 58 and an oil phase paddle 68 serving as an organic phase paddle for agitating the oil phase 60.

The vessel 18 constituting the ileum chamber is similar in structure to the vessel 16 constituting the jejunum chamber. Specifically, reference numeral 70 denotes a supply path provided to supply the liquid 56 in the vessel 16 constituting the jejunum chamber to the vessel 18 constituting the ileum chamber. The supply path 70 is provided with a peristaltic pump 72. A liquid 74 in the vessel 18 constituting the ileum chamber is also separated into an aqueous phase 76 and an oil phase 78 serving as an organic phase. The vessel 18 is similarly provided with an agitator 80 and a pH sensor 82. The agitator 80 includes an aqueous phase paddle 84 for agitating the aqueous phase 76 and an oil phase paddle 86 serving as an organic phase paddle for agitating the oil phase 78. Reference numeral 88 denotes a drain device from the vessel 18 constituting the ileum chamber.

In a test of a drug to be fully dissolved in the vessel 16 constituting the jejunum chamber, a configuration not including the vessel 18 constituting the ileum chamber may be employed.

In a test of an animal drug to be administered to an animal, e.g., a cow, a plurality of vessels 12 constituting stomach chambers may be provided, and the supply path 24 of digestive juice may be provided for each of the vessels 12 from one vessel 22 for storing the gastric juice 20 as digestive juice.

The vessels 12, 14, and the like constituting the stomach, the duodenum, and other chambers may be connected in series if needed, and the sets of the vessels connected in series may be disposed in parallel. In addition to the illustrated configuration, the supply paths 24 and 42 of digestive juice such as the gastric juice 20 and the supply paths 34, 50, and the like connecting the vessels 12, 14, and the like are easily connected to or separated from one another by using connectors or the like, so that the device configuration can be optionally changed.

The agitators 28, 46, 62, and 80 provided in the vessels 12, 14, 16, and 18 have the function of rising and lowering according to changes of the liquid levels of the vessels 12, 14, 16, and 18. In the vessel 16 constituting the jejunum chamber and the vessel 18 constituting the ileum chamber, tests may be conducted only with the aqueous phases 58 and 76. In this case, the oil phase paddles 68 and 86 may be removably provided for the agitators 62 and 80.

The device for testing solubility in FIG. 1 is controlled by a control device 90.

Figure 2:
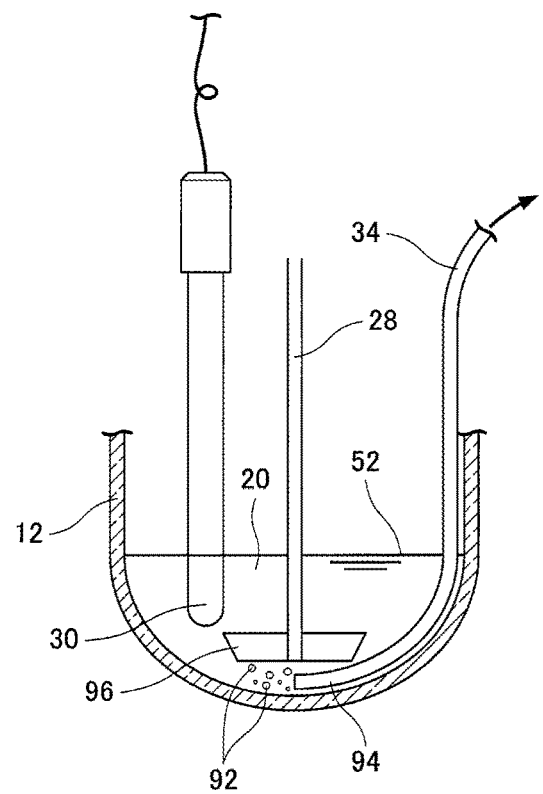
FIG. 2 is an enlarged cross-sectional view illustrating a principal part in FIG. 1.

FIG. 2 illustrates the detailed structure of the vessel 12 constituting the stomach chamber. The vessel 12 is, for example, a glass vessel. The inside of the vessel is observable from the outside. The illustrated vessel 12 is a cylinder with the spherical bottom. Ordinary oral drugs typically stay solid in fragments without being fully dissolved in the stomach. FIG. 2 illustrates drugs 92 in such a state.

The supply path 34 from the vessel 12 constituting the stomach chamber to the vessel 14 constituting the duodenum chamber is provided in the form of a suction nozzle 94 in the vessel 12 constituting the stomach chamber. The suction nozzle 94 is opened at the center of the bottom of the vessel 12. Specifically, if the vessel 12 has a spherical bottom as illustrated, the drugs 92 are collected at the center of the bottom of the vessel by the action of gravity. The suction nozzle 94 is opened so as to effectively suck the drugs 92 collected at the center of the bottom of the vessel 12.

The form of the vessel 12 is not limited to the illustrated spherical bottom. The vessel 12 may be provided in other suitable forms. For example, a flat bottom advantageously reduces interference between a paddle 96 of the agitator 28 and the suction nozzle 94. In this respect, the vessel 14 constituting the duodenum chamber or the like is similar to the vessel 12.

In either case, the suction nozzle 94 is opened at the bottom or the center of the bottom of the vessel 12, thereby fully delivering a liquid containing the drugs 92 into the subsequent vessel 14 disposed downstream of the vessel 12.

Figure 3:
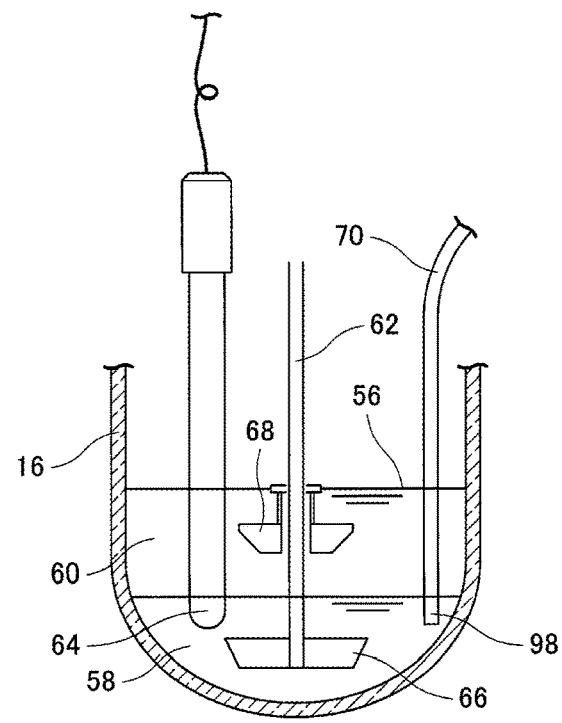
FIG. 3 is an enlarged cross-sectional view illustrating another principal part in FIG. 1.

FIG. 3 illustrates the detailed structure of the vessel 16 constituting the jejunum chamber. The vessel 16 is similar in configuration to the vessel 12 constituting the stomach chamber. In the vessel 16, oral drugs are dissolved. As has been discussed, the liquid 56 in the vessel 16 is separated into the aqueous phase 58 and the oil phase 60. As in FIG. 2, the supply path 70 is provided in the form of a suction nozzle 98 in the vessel 16.

In the supply path 50 from the vessel 14 constituting the duodenum chamber to the vessel 16 constituting the jejunum chamber, an ejector nozzle, which is not illustrated, may be provided on the downstream end in the vessel 16. The ejector nozzle is preferably capable of properly adjusting the height of the nozzle. For example, when it is necessary to supply a liquid from the vessel 14 to the aqueous phase 58 in the vessel 16, the ejector nozzle disposed near the lower end of the aqueous phase 58 can keep, in the vessel 16, a distance between the ejector nozzle and the suction nozzle 98 on the supply path 70 from the vessel 16 constituting the jejunum chamber to the vessel 18 constituting the ileum chamber. This configuration can conduct a proper solubility test. If the need for supplying a liquid to the aqueous phase 58 is eliminated or in the absence of the oil phase 60, the ejector nozzle is installed above the liquid level, allowing the confirmation of the presence or absence of clogging in the supply path 50 or the ejector nozzle. Also for the supply path 70 from the vessel 16 constituting the jejunum chamber to the vessel 18 constituting the ileum chamber, the same configuration may be used.

The oil phase paddle 68 of the agitator 62 can have a floating configuration, thereby favorably tracking changes of the levels of the aqueous phase 58 and the oil phase 60.

Figure 4:
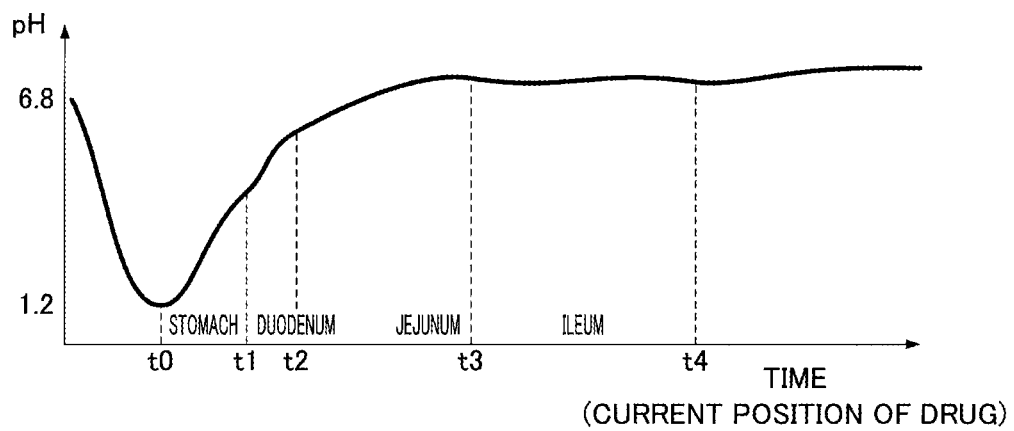
FIG. 4 indicates a transition of a pH in a human gastrointestinal tract.

The control device 90 will be described below. One function of the control device 90 is to control a pH in each vessel according to a pH in each gastrointestinal tract of a living body. FIG. 4 indicates a transition of a pH in a human gastrointestinal tract and a change of a pH around orally administered drugs. The vertical axis indicates a pH while the horizontal axis indicates an elapsed time. The oral drugs move from the stomach to the duodenum and then move to the jejunum and the ileum with time. In other words, the horizontal axis in FIG. 4 indicates a lapse of time and also indicates which organ contains the drugs 92 after a lapse of a predetermined time.

In FIG. 4, the position of the vertical axis on the horizontal axis indicates the timing of administration of the drugs into a human mouth. At this point, a pH around the drugs is 6.8. Thereafter, the drugs reach the stomach through an esophagus. t0 indicates a point of time when the drugs reach the stomach, that is, the start time of a solubility test. At this point, a pH around the drugs is 1.2. t1 indicates a time when the drugs are excreted from the stomach, t2 indicates a time when the drugs are excreted from the duodenum, and t3 indicates the time of excretion from the jejunum. t4 indicates the time of excretion from the ileum, and the solubility test is completed at this point. FIG. 4 indicates that a pH value tends to increase from the stomach to the jejunum through the duodenum.

The control device 90 controls the amount of the gastric juice 20 supplied into the vessel 12 constituting the stomach chamber and controls the amount of the intestinal juice 40 supplied into the vessel 14 constituting the duodenum chamber such that the pH of liquid in each vessel corresponds to a value indicated in FIG. 4. This can obtain a pH in each of the vessels 12, 14, 16, and 18 as in actual human gastrointestinal tract. The pH of the gastric juice 20 is set at 1.2 while the pH of the intestinal juice 40 is set at 6.3.

The control device 90 controls the amount of liquid in each of the vessels 12, 14, 16, and 18. Specifically, by using a sensor for detecting the mass of each vessel containing a liquid, a sensor for detecting the level of liquid (liquid level) in each vessel, and a sensor for detecting the flow rates of the peristaltic pumps 36, 54, and 72, the control device 90 detects the amount of liquid in each of the vessels 12, 14, 16, and 18 and controls the operations of the peristaltic pumps 36, 54, and 72 and the peristaltic pumps 26 and 44 based on the detected amount. This controls the amount of liquid in each of the vessels.

The use of the sensor for detecting the mass of the vessel, in particular, can properly control the amount of supplied liquid even in a temperature change, for example. The use of the sensor for detecting the level or flow rate of liquid can properly control the amount of the supplied liquid even if the specific gravity of the liquid is changed by mixing multiple solutions during a test. Moreover, the combined use of these sensors can properly control the amount of a supplied liquid even under complicated test conditions.

Figure 5:
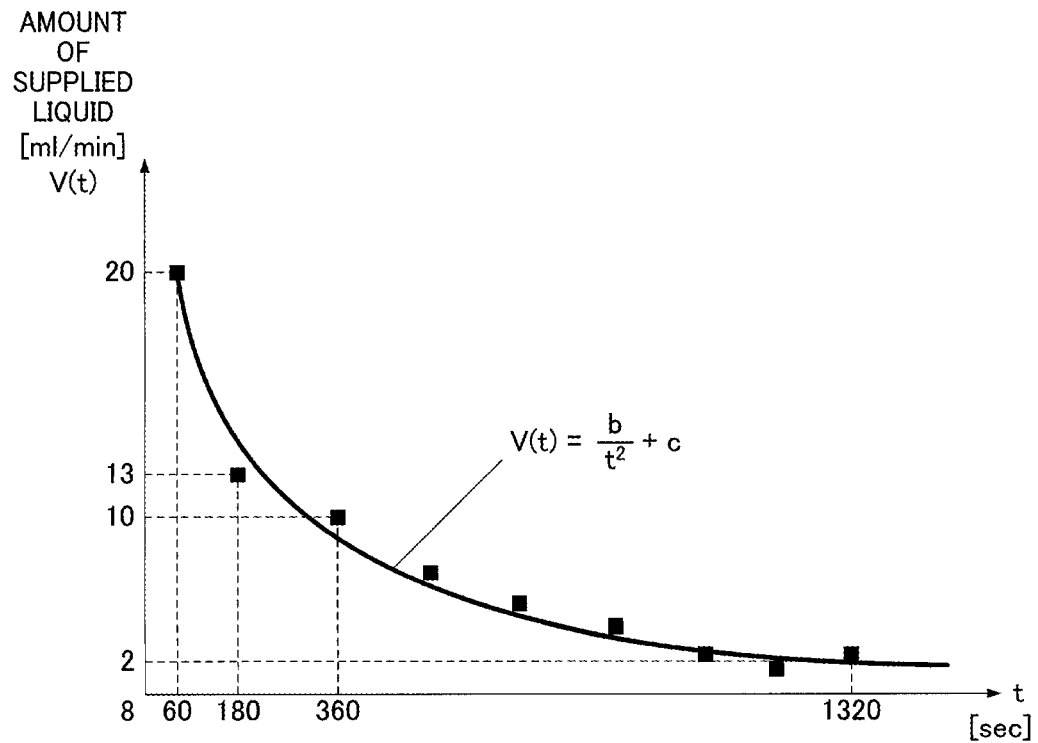
FIG. 5 indicates a value of a delivery speed of a liquid containing the drugs at each time when the drugs move in the gastrointestinal tract.

FIG. 5 indicates values of the flow rate of liquid containing the drugs, that is, the amount of supplied liquid (mL/min), in other words, a delivery speed at each time when the drugs move in the gastrointestinal tract. The vertical axis indicates a flow rate while the horizontal axis indicates a time. Unlike in FIG. 4, FIG. 5 indicates the characteristics of the respective gastrointestinal tract. As indicated in FIG. 5, the flow rate of a liquid containing the drugs forms a gradually decreasing curve. The gradually decreasing curve can be expressed by a proper mathematical expression, so that the peristaltic pumps 36, 54, and 72 can be appropriately controlled according to the expression. For the mathematical expression, various kinds of expressions can be used as approximate expressions. For example, the following expression (1) may be used:

$$V(t) = (b/t^2) + c \quad (1)$$

where $V(t)$ is a flow rate, $t$ is an elapsed time, and $b$ and $c$ are constants.

The expression is determined as follows: a flow rate, that is, an amount of supplied liquid from, for example, a human stomach to a human duodenum is known in advance according to various conditions. When the expression is used, constants b and c are determined based on the known value.

Specifically, FIG. 5 indicates a temporal change of the amount of liquid supplied from the stomach to the duodenum by the peristaltic pump 36. In FIG. 5, a temporal transition of the operation characteristics of the peristaltic pump 36 according to the known value are plotted as discrete data on the graph. For example, for the elapsed time t=60 seconds, the amount of supplied liquid is 20 mL/min. For the elapsed time t=180 seconds, the amount of supplied liquid is 13 mL/min. For the elapsed time t=360 seconds, the amount of supplied liquid is 10 mL/min. Furthermore, for the elapsed time t=1320 seconds, the amount of supplied liquid is suitably set at 2 mL/min. From this data, the constants b and c in the expression can be determined, completing the foregoing expression. Thus, characteristics required for the peristaltic pump 36 are successively defined. The peristaltic pump 36 is then controlled according to the determined expression.

The amount of liquid supplied from the duodenum to the jejunum and the amount of liquid supplied from the jejunum to the ileum are similarly controlled. In these cases, the constants b and c in the expression have different values from those of the amount of liquid supplied from the stomach to the duodenum.

For example, initial amounts of liquid in the vessels 12, 14, 16, and 18 are known and the control amount of supplied liquid is updated, for example, every one second, thereby calculating a temporal change of the amount of liquid (liquid amount) in each of the vessels 12, 14, 16, and 18 and performing control accordingly. In this case, if the volume of liquid in the vessel at time t is denoted as A(t), the volume of liquid in the vessel at time t−1, which is one second before time t1, can be denoted as A(t−1). Thus, by subtracting A(t) from A(t−1), flow rate V(t) [mL/min] at time t can be determined.

Specifically, by using an index reducing function called "primary rate equation," A(t) can be expressed as below.

$$A(t) = A_0 \times e^{-kt}$$

where $A_0$ is an initial amount, and k is a time required for reducing the initial amount $A_0$ to a half. At this point, A(t−1) can be similarly expressed as below.

$$A(t-1) = A_0 \times e^{-k(t-1)}$$

Thus, the following expression is obtained by the foregoing subtraction:

$$A(t-1) - A(t) = V(t) = A_0 \times e^{-kt} \times (e^k - 1) \quad (2)$$

In other words, expression (2) can be used instead of expression (1).

According to an initial pH value in liquid in each of the vessels 12, 14, 16, and 18, a measured value or a default value of a pH value in liquid flowing into and out of each of the vessels 12, 14, 16, and 18, and the determined amount of supplied liquid, a pH value of liquid in each of the vessels 12, 14, 16, and 18 can be determined by calculation. Based on the calculated value and the detection results of the pH sensors 30, 48, 64, and 82, advanced control can be performed by the control device 90.

By applying the foregoing control method, a volume of liquid in each of the vessels 12, 14, 16, and 18 can be also controlled by using the control device 90. Specifically, the volume of liquid in each of the vessels 12, 14, 16, and 18 can be also increased or reduced according to an actual increase or decrease of liquid in each gastrointestinal tract based on an inflow from the upstream side and an outflow to the downstream side. Alternatively, the volume can be kept constant. In the vessel 18 constituting the ileum chamber, the drain device 88 performs the same operation as an outflow to the downstream side. In addition, by introducing a device for detecting an actual volume of liquid in each of the vessels 12, 14, 16, and 18 in real time, for example, a device capable of detecting a mass, a liquid level, and an inflow/outflow amount or the like, whether the volume changes with time or remains constant at a target volume with time can be monitored all the time, at regular intervals, or at any times. If the detected result is different from a target value, the control device 90 controls the operations of the peristaltic pumps 36, 54, and 72 so as to correct the amount of supplied liquid.

As is understood from the description, the value of a liquid volume in each of the vessels 12, 14, 16, and 18 can be predicted. Thus, the monitoring of the volume allows a determination to be made on the presence or absence of trouble, for example, detection of failures of liquid supply devices such as the peristaltic pumps 36, 54, and 72 and other devices or detection of clogging in the supply paths 34, 50, and 70.

As is understood from the description, in the device for testing solubility according to the embodiment of the present invention, various values calculated and simulated offline can be inputted as test conditions to the illustrated device. The values include, for example, an amount of liquid in each of the vessels 12, 14, 16, and 18, a pH value of the liquid, an amount of liquid supplied among the vessels 12, 14, 16, and 18, an approximate expression indicating an approximate change of the amount of supplied liquid, and the constant of the expression. This configuration can conduct solubility tests on drugs under various conditions.

In the device for testing solubility according to the embodiment of the present invention, a flow rate, that is, a delivery speed in the supply paths 34, 50, and 70 can be detected by using a flowmeter or other measuring devices. With this configuration, a flow rate, that is, an amount of supplied liquid can be accurately controlled based on the detection result.

In the example of the description, the peristaltic pump is illustrated as a driving source for supplying liquid. Other kinds of pumps or other liquid-supply driving sources are also preferably usable.

Some oral drugs do not substantially dissolve in the stomach and start dissolving when reaching the small intestine. Such drugs are called enteric coated formulations. In a solubility test on such drugs, a netlike storage device such as a basket is used to ensure the arrival of drugs at the intestine through the stomach. Subsequently, the storage device containing the drugs is immersed into liquid in the vessel 12 constituting the stomach chamber, and then the storage device is removed therefrom and is immersed into liquid in the vessel 14 constituting the duodenum chamber. The same operation is repeated for the subsequent stages in the small intestine until the drugs are fully dissolved.

The device for testing solubility according to the embodiment of the present invention can simulate the gastrointestinal tract of a living body, e.g., a human being as correctly as possible and measure, according to the actual conditions, an absorption rate for drugs less likely to be dissolved in gastrointestinal tract. Moreover, the drugs from the vessel 12 corresponding to the stomach can be fully excreted by the nozzle 94. The amount of liquid in the vessel 14 corresponding to the duodenum and the liquid levels of the aqueous phases 58 and 76 in the vessels 16 and 18 corresponding to the jejunum and the ileum can be kept constant or can be changed as needed.

The invention claimed is:

1. A device for testing solubility of drugs in gastrointestinal tract, the device comprising:
    a plurality of vessels respectively corresponding to gastrointestinal tract of a living body;
    a digestive-juice supply device supplying digestive juice to at least one of the vessels requiring supply of the digestive juice;
    a liquid delivery path provided between the vessels and extending from the vessel on an upstream-side to the vessel on a downstream-side;
    a delivery driving source applying a fluid force to a mixed liquid of the digestive juice and an oral drug in the liquid delivery path;
    a control device controlling a delivery speed of the delivery driving source according to a temporal change of a flow rate from an upstream side to a downstream side of the gastrointestinal tract of the living body; and
    a suction nozzle that communicates with the liquid delivery path and is opened at a bottom of the upstream-side vessel so as to be able to fully deliver the oral drug in the upstream-side vessel into the downstream-side vessel.

2. The device for testing solubility of drugs in gastrointestinal tract according to claim 1, wherein the control device controls the delivery speed of the delivery driving source according to a temporal change of a speed of excretion from the gastrointestinal tract of the living body.

3. The device for testing solubility of drugs in gastrointestinal tract according to claim 1, wherein the control device controls an amount of liquid in each of the vessels with time by controlling the delivery speed of the delivery driving source.

4. The device for testing solubility of drugs in gastrointestinal tract according to claim 3, further comprising a liquid amount sensor for detecting the amount of liquid in each of the vessels.

5. The device for testing solubility of drugs in gastrointestinal tract according to claim 3, wherein a most downstream vessel is provided with a drain device for controlling an amount of liquid in the most downstream vessel with time.

6. The device for testing solubility of drugs in gastrointestinal tract according to claim 3, wherein the control device determines presence or absence of trouble in the device based on the amount of liquid in each of the vessels.

7. The device for testing solubility of drugs in gastrointestinal tract according to claim 1, wherein the device for testing solubility is capable of inputting, as a test condition, an offline calculation result of at least one of an amount of liquid in each of the vessels, a pH value in each of the vessels, and a flow rate from the upstream side to the downstream side.

8. The device for testing solubility of drugs in gastrointestinal tract according to claim 1, further comprising a delivery speed detector for detecting the delivery speed of the delivery driving source,
    wherein the control device controls the delivery speed of the delivery driving source based on a detection result obtained by the delivery speed detector.

9. The device for testing solubility of drugs in gastrointestinal tract according to claim 1, further comprising an agitator for agitating liquid in each of the vessels,
    wherein the agitator is relocatable according to a change of an amount of liquid in each of the vessels.

10. A device for testing solubility of drugs in gastrointestinal tract, the device comprising:
    a plurality of vessels respectively corresponding to gastrointestinal tract of a living body;
    a digestive-juice supply device supplying digestive juice to at least one of the vessels requiring supply of the digestive juice;
    a liquid delivery path provided between the vessels and extending from the vessel on an upstream-side to the vessel on a downstream-side;
    a delivery driving source applying a fluid force to a mixed liquid of the digestive juice and an oral drug in the liquid delivery path; and
    a control device controlling a delivery speed of the delivery driving source according to a temporal change of a flow rate from an upstream side to a downstream side of the gastrointestinal tract of the living body,
    wherein a vessel corresponding to a small intestine of the living body contains a liquid having an organic phase and an aqueous phase, the vessel corresponding to the small intestine is provided with an agitator for agitating the liquid in the vessel, the agitator includes an organic-phase paddle and an aqueous-phase paddle, and the organic-phase paddle is a floating paddle.

11. A device for testing solubility of drugs in gastrointestinal tract, the device comprising:
    a plurality of vessels respectively corresponding to gastrointestinal tract of a living body;
    a digestive-juice supply device supplying digestive juice to at least one of the vessels requiring supply of the digestive juice;
    a liquid delivery path provided between the vessels and extending from the vessel on an upstream-side to the vessel on a downstream-side;
    a delivery driving source applying a fluid force to a mixed liquid of the digestive juice and an oral drug in the liquid delivery path;
    a control device controlling a delivery speed of the delivery driving source according to a temporal change of a flow rate from an upstream side to a downstream side of the gastrointestinal tract of the living body; and
    a netlike storage device,
    wherein the storage device containing a drug to be undissolved in a stomach of the living body immerses the drug into the digestive juice in a vessel corresponding to a stomach of the living body, the storage device containing the drug conveys the drug from the vessel corresponding to the stomach of the living body to a vessel corresponding to a small intestine of the living body, and then the storage device immerses the drug into the digestive juice in the vessel corresponding to the small intestine of the living body.

* * * * *